United States Patent [19]

Nash

[11] Patent Number: 4,813,266

[45] Date of Patent: Mar. 21, 1989

[54] METHOD AND APPARATUS FOR COMPUTING SURFACE COEFFICIENTS OF FRICTION

[76] Inventor: Patrick L. Nash, 9506 Autumn Gold, San Antonio, Tex. 78250

[21] Appl. No.: 98,928

[22] Filed: Sep. 21, 1987

[51] Int. Cl.$^4$ .............................................. G01N 19/02
[52] U.S. Cl. ........................................... 73/9; 73/489; 364/556
[58] Field of Search ........................... 73/9, 865.3, 489; 364/566, 556

[56] References Cited

U.S. PATENT DOCUMENTS

| | | | |
|---|---|---|---|
| 4,212,063 | 7/1980 | Härdmark | 364/426 |
| 4,490,802 | 12/1984 | Miller | 364/567 |
| 4,594,878 | 6/1986 | Abe et al. | 73/9 |
| 4,745,564 | 5/1988 | Tennes et al. | 364/566 |

FOREIGN PATENT DOCUMENTS

| | | | |
|---|---|---|---|
| 0153088 | 12/1979 | Japan | 73/9 |
| 0838527 | 6/1981 | U.S.S.R. | 73/9 |

*Primary Examiner*—Parshotam S. Lall
*Assistant Examiner*—S. A. Melnick
*Attorney, Agent, or Firm*—Arnold, White & Durkee

[57] ABSTRACT

A microprocessor-based interactive apparatus to compute coefficients of static and dynamic friction for a test surface using deceleration data of a weighted block sliding to a rest on the test surface. The apparatus provides an accessible graphical display of the recorded deceleration data which comprises a series of relative time values and associated block acceleration values. A movable cursor permits the user to interactively select the point on the surface for which the coefficient of friction is to be computed. The computed coefficient is then displayed on the graphics display device with the deceleration plot. The cursor may then be redisplayed and moved horizontally with respect to the graphical plot of the deceleration data so that another coefficient of friction may be computed and displayed for a different selected point.

15 Claims, 2 Drawing Sheets

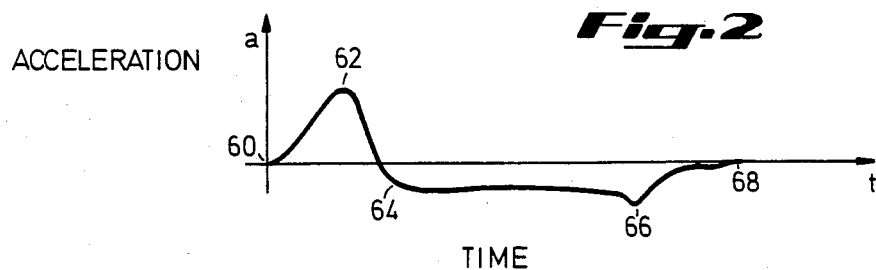
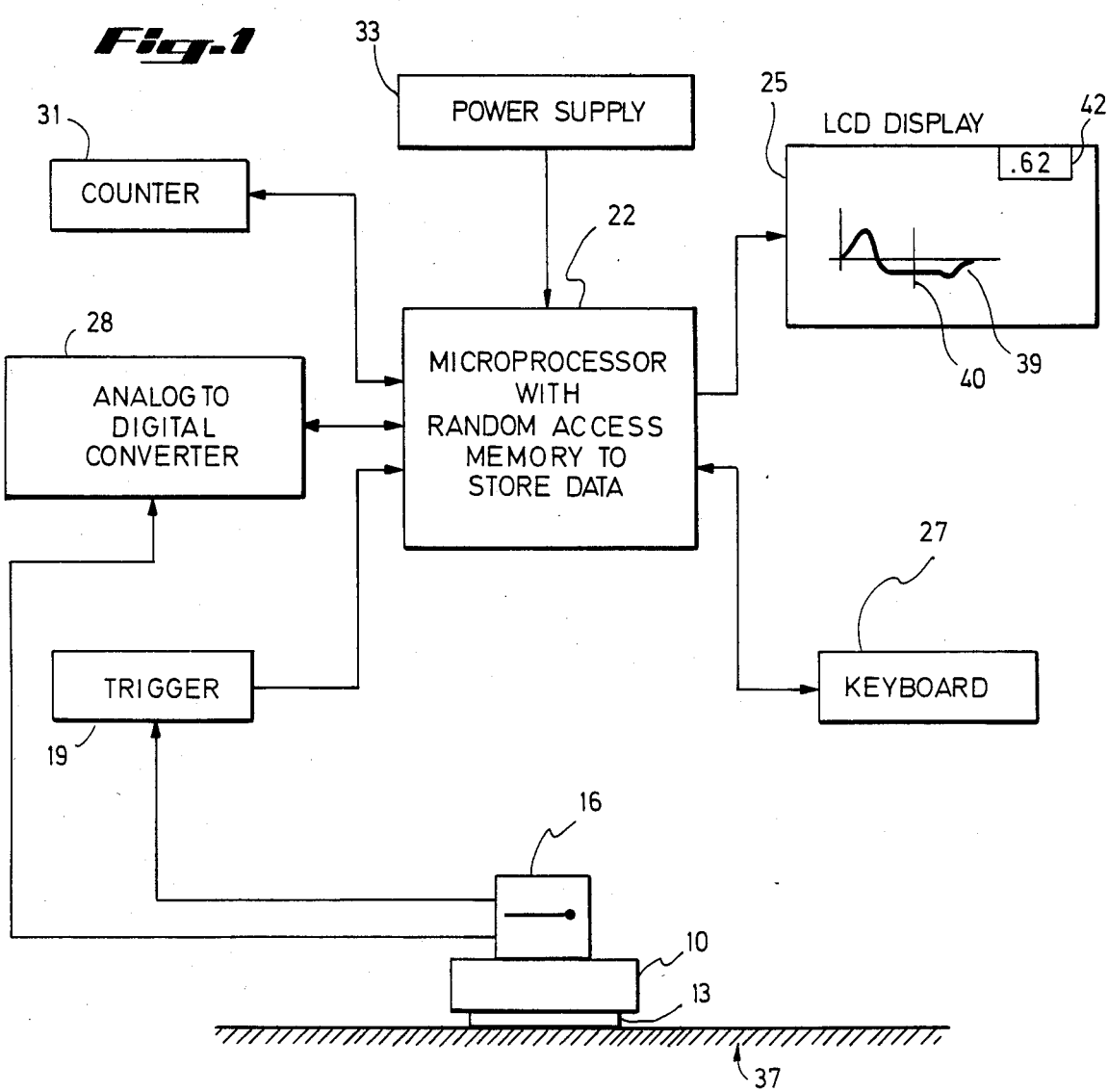

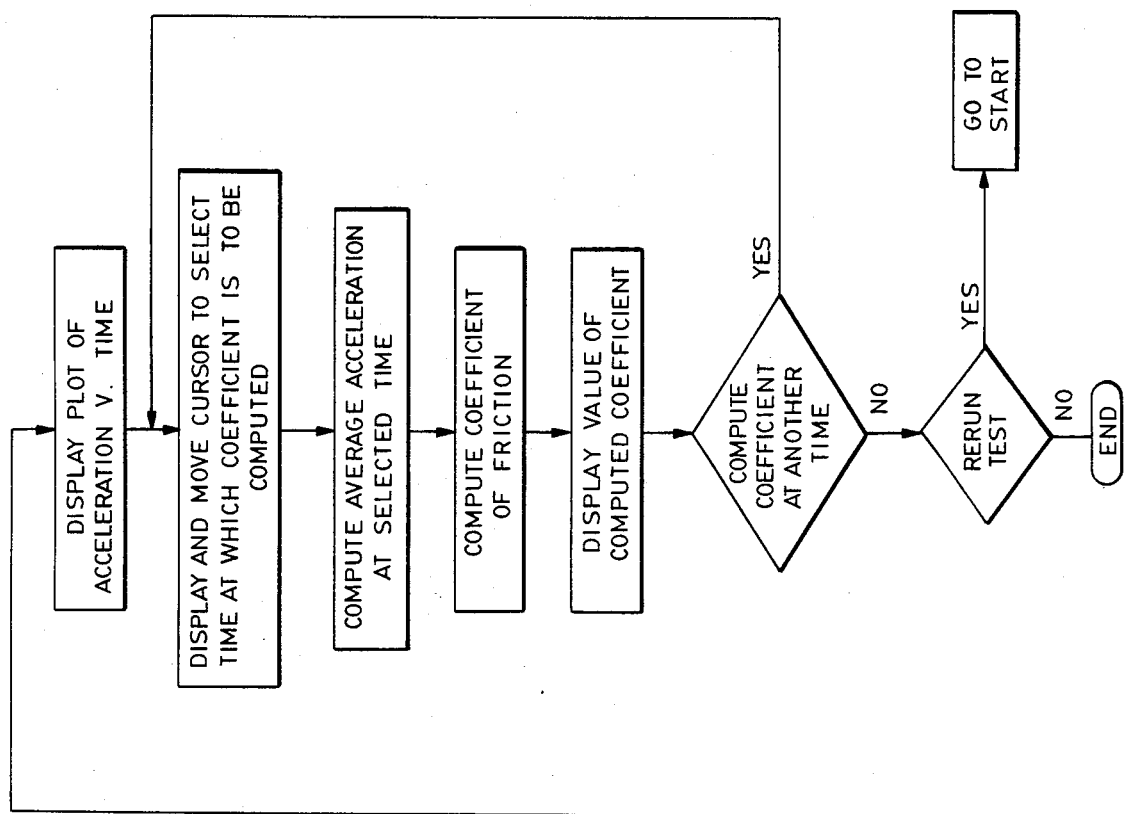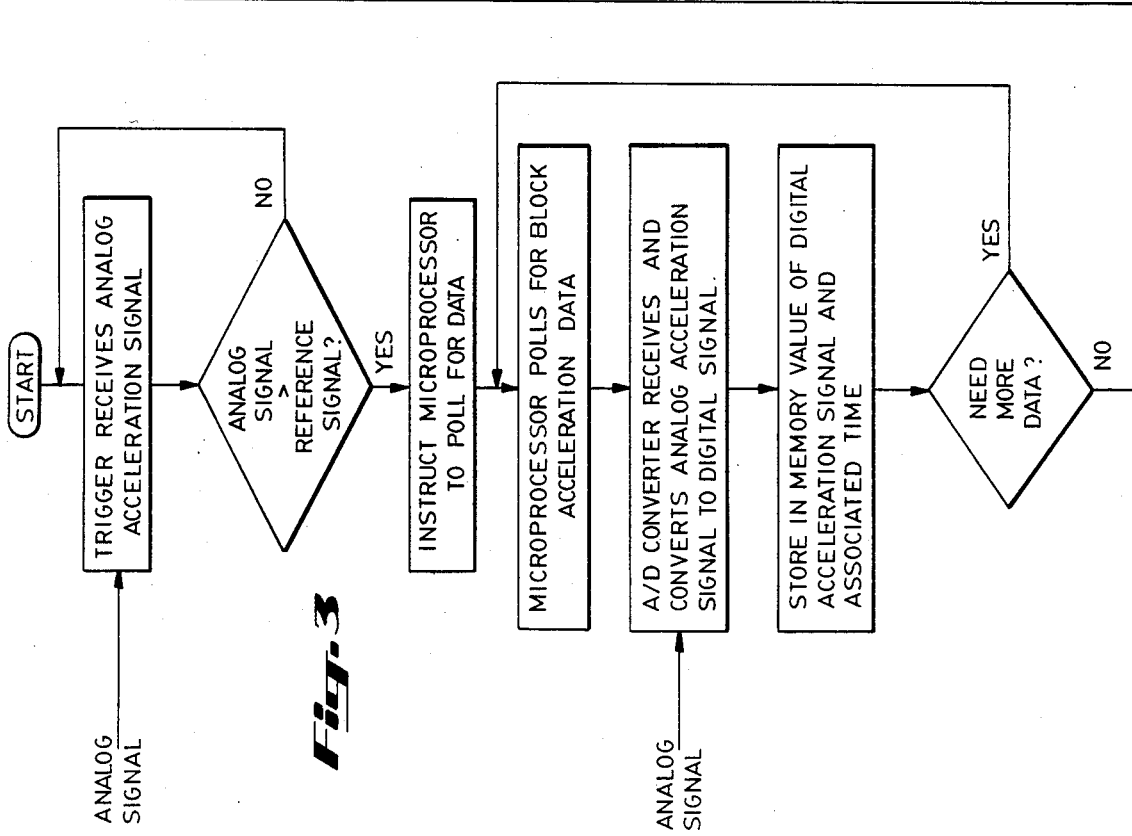
Fig. 3

METHOD AND APPARATUS FOR COMPUTING SURFACE COEFFICIENTS OF FRICTION

BACKGROUND OF THE INVENTION

The present invention relates to a method and apparatus for determining coefficients of friction. More particularly, the invention pertains to a microprocessor-based apparatus for receiving, and plotting on a visual display device, signals proportional to the acceleration of a block on a test surface, selecting a time point one or more times at which the coefficient of friction is to be computed, and displaying the computed coefficient.

Two bodies in contact experience mutual frictional forces. The force of kinetic friction operates when the body surfaces are moving relative to one another, while the force of static friction acts on bodies which are stationary with respect to each other. A block at rest on a surface may be placed in motion by applying a force to the block to overcome the static friction which keeps the block at rest. The maximum force of static friction will be the same as the smallest force necessary to start the block in motion. Once motion has started, this same amount of force produces an accelerated motion on the block since the frictional forces acting between the relatively moving surfaces usually are lower than static forces. A smaller applied force than that necessary to start a body in motion may keep the block in uniform motion without acceleration. This small applied force is equal in magnitude but opposite in direction to the force of kinetic or dynamic friction which is the resisting force between two relatively moving surfaces when that movement is occurring without interruption.

The coefficients of friction provide an indication of the degree of slipperiness between the two contacting surfaces. The coefficient of static friction is computed as the ratio of the magnitude of the maximum force of static friction to the magnitude of the normal force. The normal force is that force which a body exerts on the surface on which the body rests. For a block resting on a horizontal table or sliding along it, the normal force is equal in magnitude to the weight of the block. The coefficient of kinetic friction is computed as a ratio of the magnitude of the force of kinetic friction to the magnitude of the normal force. Generally, the coefficients of friction are values less than 1, and generally the static coefficient of friction exceeds the kinetic coefficient of friction.

There is a need in many circumstances to determine a surface's degree of slipperiness. Typically in the building construction industry, contractors are interested in knowing whether surfaces on which people are to walk are safe. Also, situations involving slip and fall accidents may require test analysis to determine whether the surface on which an individual fell could be considered dangerous. Manufacturers of floor polishes are also interested in safety testing surfaces coated with floor polishes being considered for marketing.

The results of slipperiness tests for surfaces are compared with established standards to determine if the surface is dangerous. The National Bureau of Standards established in 1948 a standard for the kinetic coefficient of friction. Research paper RP1879 reported that a slippery condition existed for a surface being tested if the coefficient of friction was less than 0.40.

The American Society of Testing and Materials established a standard that a static coefficient of friction of 0.50 or above is considered safe for a dry walkway surface. This standard is described in ASTM Standard D 2147-75. Various publications by the National Bureau of Standards recognize this 0.50 standard, and it is reported that the Underwriters Laboratories adopted this as an industry standard.

Generally, the static anti-slip coefficient of friction values have these meanings.

| Coefficient | Condition |
| --- | --- |
| .60 or above | very safe |
| .50 to .59 | relatively safe |
| .40 to .49 | dangerous |
| .35 to .39 | very dangerous |
| .00 to .34 | unusually dangerous |

A value below 0.50 means that the surface may be considered dangerous to walk on. The higher value indicating safety for static coefficients is valid since test results usually are higher for static than dynamic values obtained during tests of dry surface conditions.

Several known methods and apparatus have been used to determine the coefficients of friction of a surface. Some have provided information to determine the static coefficient, while others provided information to determine the kinetic coefficient. Since the concern primarily has involved the slipperiness of walkway and walking surfaces, these various devices have used a standard known surface to rest or slide on the surface to be tested. This standard surface has been a flat sanded smooth strip of shoe sole leather.

One such device to measure the coefficient of kinetic friction was developed during the 1940's and employed a pendulum. A strip of shoe leather was attached to the bottom of a weighted block rigidly suspended from a pivot point. A pointer extending from the pivot was attached to the pendulum. The block was raised arcuately to a predetermined height and released. The block swung along an arc towards and over the surface to be tested. After the block slid across the test surface, it continued its arcuate swing upward. The pointer moved upwardly with the block over an arcuately shaped gauge. The coefficient of kinetic friction could be computed using information from the gauge or from knowing the difference between the starting height and the height the block reached in its arcuate swing. This device, however, was not reliable because a portion of the energy was absorbed when the block struck the test surface at the bottom of the pendulum swing. Thus, the block having the shoe leather had to be carefully positioned over the test surface. Also friction created by the pendulum moving the pointer needle affected the results.

A second method used a machine having an articulated strut. A weight was pivotally connected to the upper end of a vertically disposed strut. The bottom of the strut was pivotally connected to a block which had a bottom lining of the test shoe leather. The leather rested on the surface to be tested. An increasing lateral force was applied to the block by rotating the strut until a slip of the block occurred. The coefficient of static friction could then be determined by finding the ratio of the lateral force to the known vertical force imposed by the weight at the upper end of the strut.

A third type of machine which measures the coefficient of friction involved dragging a block over the test surface. The block had a known weight and the bottom surface was lined with the test shoe leather. A force meter connected to the block measured the lateral pull necessary to begin movement of the block. That measurement permitted determination of the static coefficient of friction. Continued pulling of the spring kept the block in motion and sliding across the test surface. The amount of force necessary to keep the block in motion permitted determination of the coefficient of dynamic or kinetic friction.

These various devices, however, have limitations. One problem is that the different types of devices have yielded different results for the same surface. To properly evaluate the test results, one must be familiar with the type of equipment used and the effect on test results which arise from the various mechanical linkages involved in the apparatus.

Calibration of these testing machines is critical as well. Present test machines are generally difficult to calibrate against a national standard because of their inherent inaccuracies. Calibration involves using the machine on a surface, usually tile, having a known coefficient of friction.

Known types of friction meters also have had problems with accuracy and reproducibility of measurements and reliability of test results. For instance, in determining the coefficient of static friction, uncertainties arise when the stretching distances of the spring are measured. It is also time consuming to set up and carry out the number of tests necessary to provide confidence in the test results. It is likely that insufficient data is typically collected to obtain a suitable average for a friction coefficient. A large number of tests further may alter the characteristics of the surface being tested. Other errors are introduced when the kinetic coefficient of friction is measured. Traditional slip meters such as the drag type machine require pulling a block at a constant speed, since under ideal conditions the dynamic friction force equals the tension on the pulling string. The tension is measured with a spring balance. This approach leads to results that are reliable to only 10 or 15 percent, and are difficult to reproduce by other observers.

Faulconer U.S. Pat. No. 4,387,587 issued to describes an apparatus and processing methodology for acquiring the deceleration data of a motor vehicle which is skidding over a road surface to a stop. The device mounts to a car and in operation acquires data that may be used to determine the length of the skid and the kinetic coefficient of friction between the road surface and the skidding car.

The test apparatus described in the Faulconer reference includes an accelerometer which mounts to the car for sensing the deceleration of the car during a skid. (Since the car is slowing, the acceleration is negative and decreasing, and may be referred to as deceleration.) An analog signal proportional to the deceleration is generated at periodic intervals. This signal is converted to a digital value, i.e., digitized, and communicated to a microprocessor. The digitized value is stored together with an associated time value, and is subsequently used in computing the kinetic coefficient of friction, as well as computing other parameters related to the skidding of the car. Faulconer states that the values of acceleration and time may be recorded magnetically by a suitable recorder for computer processing at a later time, and that the data may be displayed on an x-y coordinate graphic mechanism.

SUMMARY OF THE INVENTION

The present invention provides a simple and reliable way to determine the coefficients of static and kinetic friction at a specific place on the test surface. It provides an interactive means to focus attention on the specific portion of the surface for which the coefficient is to be computed. Thus, the coefficient of friction may be determined at a localized point, e.g., within a few centimeters of a selected point on a surface.

The present invention more particularly provides an interactive microprocessor-based apparatus which may be used to acquire data reflecting the slipperiness for a floor surface by using a weighted block having a bottom surface of a standard test material. The frictionometer according to the invention, being portable, may be used directly in grocery stores, factories or other slip and fall locations. It may also be used in a test lab for testing a variety of surfaces. Typically, the surface area to be tested is small and generally is no larger than several square centimeters. Apparatus of the invention can determine coefficients of friction for a specific few square centimeters of area on these surfaces. The present invention therefore provides a significant level of reliability for determining the coefficient of friction at a particular small location or surface area. The test performed by the apparatus may be replicated relatively easily and quickly to provide a confidence level for the results. Further, the technician operating the apparatus according to the present invention may select a specific point on the test surface for which the coefficient of friction is to be determined.

The invention provides a portable device to acquire, store, and analyze digitized data representing the acceleration (positive and negative) of a test block skidding across a test surface. This microprocessor based apparatus includes a test block, an accelerometer, a converter to convert analog signals to digital signals, and a graphics display device. The microprocessor communicates with an external read only memory which contains the computer program to operate the apparatus, a random access memory in which to store the deceleration data, and a keyboard with which to communicate with the microprocessor. Once the block is placed in motion across the test surface, the microprocessor receives and records deceleration data related to movement of the block on the surface. This movement is analyzed and a plot of the deceleration data is shown on the graphic display device. Using the recorded data, the coefficient of friction for the surface may be determined. The coefficient of kinetic friction or of static friction may be computed depending on the data collected and depending on what point is selected at which the coefficient is to be computed.

Apparatus according to the invention provides to a user an accessible graphical display of recorded deceleration data for a block having an industry standard surface skidding across a test surface. These data comprise a series of time values and associated block acceleration values. The data are collected and stored in the memory of the microprocessor operating under control of a computer program. The accessible graphical display permits the engineer or other individual testing surfaces to select the point on the surface for which the coefficient of friction is to be computed. The selection capability is accomplished by graphing on a display device, such as a liquid crystal output device, a plot of the block's acceleration against time. Once the recorded data are displayed, the computer program operating the apparatus may be instructed to display on the graph a cursor. Using keyboard commands, the cursor may be moved back and forth on the plot. A preferred vertical cursor intersects the curve of graphed data, and the user may use that cursor to spot or select a time point on the graph at which the coefficient of friction is to be computed.

In preferred embodiment, moving the cursor to the selected time point commands the microprocessor to select the point where the cursor is located. The computer program locates that selected point in the group of recorded deceleration data. A number of data points following the selected data point are then used to compute the average coefficient of friction. Preferably, the number of data points used in computing the average acceleration will be about 16, although this number may be varied depending on the accuracy desired and the number of data points recorded per second as the test block skids on the test surface. In an alternate embodiment, the computer program uses the selected point as the middle and takes about the same number of data values on either side of the selected point. In another alternate embodiment, the moving of the cursor and the selecting of a data point may be separate steps having separate keyboard commands.

Once the coefficient of friction is computed, its value is preferably displayed on the liquid crystal output device next to the plotted curve. The user may then rerun the test, or redisplay the cursor to select another data point at which to compute the coefficient of friction.

BRIEF DESCRIPTION OF THE DRAWINGS

FIG. 1 is a schematic diagram of the apparatus according to the present invention;

FIG. 2 is a typical plot of acceleration against time for a block sliding over a surface in response to an applied force; and FIG. 3 is a flow chart illustrating the data flow and logic process of the present invention.

DESCRIPTION OF THE PREFERRED EMBODIMENTS

With reference to FIG. 1, the present invention includes a block 10 having a known weight. Attached to the bottom of the block 10 is a strip of test shoe leather 13. An accelerometer 16 is also fixed to the block 10.

A microprocessor 22 communicates with a display device 25 and a keyboard 27. The microprocessor 22 includes or interfaces with (i.e., connects to and communicates with) appropriate read only memory, random access memory and a communications bus to transmit information between the converter 28 and the microprocessor 22 and between the microprocessor 22 and the display device 25. Wires or leads connect the accelerometer 16 through an instrumentation amplifier 27 to an analog-to-digital converter 28. The apparatus also includes a counter 31, a trigger 19, and a power supply 33.

The components of the present invention may be packaged in a portable container so that the coefficient of friction test apparatus, or frictionometer, may be conveniently carried to the surface location to be tested, e.g., the supermarket floor of a slip and fall accident.

To operate the frictionometer, a strip of shoe leather which meets national test standards is secured to the bottom surface of the block 10. The standard test material is shoe sole leather which is prepared by sanding the leather to a flat, smooth surface. Federal Test Method 7121 calls for the use of shoe leather which meets federal specification KK-L-165 leather.

The equipment is connected together for operation of the apparatus to test a surface. Appropriate wires which communicate the analog signals from the accelerometer 16 to the instrumentation amplifier 27 are connected. The trigger 19, the analog-to-digital converter 28, the video display 25 such as a liquid crystal display, the keyboard 27, and the counter 31 are connected to the microprocessor 22. A preferred embodiment uses an Intel 8088 microprocessor and the computer application program is written in machine language. The microprocessor 22 interfaces with a read only memory in which is recorded the computer program which operates the data reception and recording processes and which controls the display and analysis of the recorded data. The microprocessor 22 also interfaces to an external random access memory in which to store the associated time and block deceleration data. The counter 31 (such as an 8253 counter available from Intel, or equivalent) functions as a clock, and provides timing signals to the microprocessor 22 to time the periodic intervals for accepting a deceleration value from the accelerometer. The counter 31 also performs timing functions which assist the horizontal and vertical synchronization for the graphic display device 25 to show the graphed data.

The block 10 is placed on a test surface 37 and given an impulse to put the block 10 in motion. The impulse preferably is imparted by using a hammer to strike the side of the block. Alternatively, a weight may be suspended from a frame which is placed over a test surface so that the weight is hanging perpendicular to the test surface adjacent to the side of the block. The weight is raised and allowed to swing arcuately to strike the side of the block. The force striking the block should be sufficient to overcome the static friction holding the block at rest on the surface. The block breaks free from the surface, and begins moving with only the force of gravity and the kinetic friction force acting on the block.

As the block 10 skids on the test surface, the force of gravity pulls the block 10 downward. The kinetic friction forces acting between the block 10 and the test surface begin slowing the block 10. As the block 10 slows to a stop, the static friction force again begins to act and the block stops.

Once the power supply is switched on and the apparatus activated, the accelerometer begins generating a signal which is proportional to the acceleration of the block 10. This analog signal from the accelerometer 16 is relatively weak. The instrumentation amplifier 27, such as an AD624 amplifier available from Analog Devices in Houston, Tex., receives the accelerometer signal and amplifies it between about 100 and about 500 times. A potentiometer (not illustrated) is used to adjust the gain to provide full screen deflection; that is, the gain is adjusted so that the graphics display device displaying the digital values uses as much of the vertical space on the device as possible. This results in increased resolution of the acceleration response curve plotted on the display device. The amplified signal is communicated from the amplifier 27 to the trigger 19 and to the analog-to-digital converter 28. The trigger 19 in a preferred embodiment is a Model TLC3721P voltage comparator deveice which may be obtained from Texas Instruments or an equivalent available from other companies. The trigger 19 constantly compares the incoming analog signal with a reference signal communicated from the power supply 33. If the incoming signal is less than the reference signal, the trigger 19 outputs a low or zero voltage signal to the microprocessor. Initially, when the block is at rest, the incoming signal is less than the reference signal. Once the incoming signal exceeds the reference signal, (i.e., the block is in motion) the trigger 19 switches and generates a high voltage signal. A preferred embodiment generates a five volt signal which is communicated to the microprocessor 22. The microprocessor 22 then begins polling the analog-to-digital converter 28 for digitized values of the block's acceleration. Thus, the trigger 19 acts as a switch to detect that the block is in motion and to instruct the microprocessor to begin receiving and recording the deceleration data.

While the block 16 is at rest, the acceleration signal value sent by the accelerometer is substantially constant and is about equal to zero. After the block 10 is struck by a hammer, or by other means to impart a force, the acceleration increases rapidly. As explained above, the trigger 19 instructs the microprocessor 22 to begin receiving and recording the acceleration data. The counter 31 functions as a clock for the microprocessor 22 so that the microprocessor 22 polls the analog-to-digital converter 28 at periodic intervals for digitized deceleration data.

As explained previously, the amplified analog signal from the accelerometer 16 is communicated to the converter 28. A preferred embodiment uses the 12-bit AD574 converter available from Analog Devices in Houston, Tex.. The converter 28 converts the analog signal into a digital value. When polled by the microprocessor 22, the converter 28 communicates the current digital value of the deceleration of the block 10 to the microprocessor 22. Transmission of this data occurs on the communications bus of a microprocessor 22. The microprocessor 22 records in the random access memory the relative time and its associated acceleration value received from converter 28. Using the timing provided by the counter 31, the microprocessor 22 continues to poll the converter at periodic intervals for digitized values of deceleration. The time and deceleration data values continue to be recorded until the block 10 comes to a rest and the maximum number of permitted values are received. A preferred embodiment of the present invention records 8,192 pairs of time and acceleration values. A preferred embodiment receives and stores about 1,000 converted signals per second. For other embodiments, there may be recorded a fewer or a greater number of acceleration signals per second. Additional memory will normally permit storing a greater number of data values.

After the pairs of data are recorded, the microprocessor 22 displays on a graphic output device 25 an x-y plot 39 of the recorded time and acceleration values. A preferred embodiment uses a liquid crystal display of a type available from Sharp Electronics. The counter 31 provides timing signals for the liquid crystal display. A movable cursor may be displayed on the plot and maneuvered by the technician using keyboard commands. A preferred embodiment displays a vertical cursor 40 which intersects the graph and may be moved horizontally across the graph on the graphic device 25.

Commands entered to the microprocessor 22 from the keyboard 27 cause the vertical cursor 40 to move horizontally over the display and be positioned at a user selected time with respect to the plot 39. In a preferred embodiment, the command entered to the microprocessor 22 to position the cursor is a value between 0 and 255. This range of values corresponds to the horizontal axis of the graphics display device where "0" corresponds to the coordinate on the left side of the screen showing acceleration before the block is placed in motion and "255" corresponds to the coordinate on the right side of the screen after the block has returned to rest. Entering a numerical value to the microprocessor positions the cursor a proportional distance across on the plotted acceleration graph on the screen. For instance, entering "127" positions the cursor approximately in the middle of the plot. In an alternate embodiment, separate commands may be used to position the cursor horizontally with respect to the deceleration graph and a separate command may be then executed to select the point in time at which the coefficient of friction is to be computed.

Once the point is selected, the microprocessor locates that point in the random access memory. An average acceleration for the block 10 at the selected time is computed using a plurality of acceleration values following the selected time. A preferred embodiment uses the next 16 acceleration values to compute the average acceleration of the block 10 at the selected time. The coefficient of kinetic friction is then determined by dividing the computed average acceleration of the block 10 by the acceleration of gravity. That value is about 32.174 feet per second squared, so dividing by 32.174 provides a reasonably accurate coefficient of friction. The computed coefficient value is then displayed 42 on the graphic output device 25. The engineer or technician testing the slipperiness of a surface may display the vertical cursor 40 again in order to compute the coefficient of friction at a different point. A preferred embodiment of the present invention employs a liquid crystal display on which to plot the time and acceleration data. Other display devices may also be used with the invention.

With reference to FIG. 2, the force acting on the block 10 and the movement of the block 10 may be described graphically. At 60 the block 10 is at rest and sitting on a test surface for which the coefficients of friction are to be determined. An impulse is imparted on the block 10, and the acceleration increases to a maximum 62 when the block 10 breaks free of the test surface. The impulse force is removed and only the force of gravity and the frictional forces between the surfaces are acting on the block 10. The acceleration rapidly falls to a negative value and remains substantially constant 66 over the time that the block 10 is skidding and slowing on the test surface. Just as the force of kinetic friction slows the block 10 to a rest, the static friction force again begins to act 68 on the block 10. Graphically this is portrayed as a sharp decrease 66 in the force acting on the block 10. As the block 10 stops moving, the acceleration curve 70 returns to zero.

FIG. 3 is a flowchart illustrating the data flow and logic process of the present invention for acquiring and analyzing acceleration data from a surface. The test shoe leather 13 is affixed to the bottom of the block 10 which is placed on the surface 37 to be tested. The apparatus is activated by switching on the power supply 33. The accelerometer 16 begins generating an analog signal proportional to the acceleration of the block 10. The analog signal is communicated to the trigger 19 which compares the incoming signal with a reference signal from the power supply 33. An analog signal which is greater than the reference signal indicates that the block 10 has been struck and placed in motion on the test surface 37. Once the trigger 19 determines that the block 10 is in motion, the trigger 19 generates a signal which is communicated to the microprocessor 22. The trigger 19 thus acts as a switch to instruct the microprocessor 22 to poll the analog to digital converter 28 for digitized values of the block's acceleration. It is noted that the analog signal from the accelerometer 16 is communicated through the amplifier 27 to both the trigger 19 and the analog-to-digital converter 28, but for purposes of the FIG. 3 flowchart, that communication is not illustrated.

Once the microprocessor 22 is instructed to poll for acceleration data, the trigger 19 has served its purpose. The analog-to-digital converter 28 receives the amplified analog signal from the accelerometer 16. That signal is converted to a digital signal and that digital signal is communicated to the microprocessor 22. The microprocessor 22 stores in a random access memory the value of the digital acceleration signal and its associated time interval relative to the trigger switching and instructing the microprocessor 22 to begin polling for data. The computer program used in a preferred embodiment continues polling for acceleration data until a predetermined number of data points have been digitized, received by the microprocessor 22, and stored.

When a sufficient number of data points are collected, the computer program instructs the microprocessor 22 to display a plot 39 of the recorded acceleration against time on a graphics display device 25. A typical plot of such data is illustrated in FIG. 2. Once the plot 39 is displayed, a cursor 40 is displayed on the plot 39 and the user enters a command to move the cursor 40 and to select the time point at which the coefficient of friction is to be computed. With the cursor 40 positioned over a time point, the computer program relates the horizontal position of the cursor 40 to a time value recorded in its random access memory. A preferred embodiment of the present invention uses the next 16 acceleration values to compute the average acceleration of the block 10 at the selected time. The computed average acceleration of the block 10 at the selected time is then divided by the average acceleration of the force of gravity to determine the coefficient of friction at the selected point. The computed coefficient 42 is then preferably displayed on the graphics display device 25. The user may then elect to compute the coefficient at another time and enter an appropriate command to the computer program to display and to move the cursor 40 to the new point at which the coefficient is to be computed. If a coefficient of friction at a new point is not to be computed, the user may rerun the test or end the program.

Various models of accelerometers well known in the art are useful with the invention. These accelerometers may be broadly grouped into two categories or types. One type of accelerometer is responsive to high frequencies and is able to track and monitor fast changes in acceleration. These types of accelerometers, however, are less satisfactory in tracking substantially constant acceleration and when doing so, may generate spurious or inconsistent signals. A second type of accelerometer provides accurate tracking of substantially constant acceleration but are less responsive to fast changes in acceleration. Spurious signals may be generated by this type of accelerometer when tracking fast changes in acceleration.

The former accelerometer is more useful in reporting the occurrence and magnitude of the sudden slight dip in acceleration which occurs when the static forces of friction begin acting on the sliding block moments before the block comes to a rest. The latter accelerometer is more useful in sensing the displacement of the sliding block on the surface. An alternate embodiment of the present invention may include both types of accelerometers, and thus, the microprocessor would receive two acceleration signals. In this instance, the computer program has to evaluate both sets of signals to eliminate the spurious data. One embodiment may use the output from a low frequency accelerometer to trigger operation of the second, high frequency accelerometer. Another embodiment may monitor the spurious high frequency output signal and detect the sharp pulse generated when the rapid change in acceleration due to static friction occurs. The result of such analysis and evaluation can be a composite graph from the two sets of data such as that shown in FIG. 2. Given time and acceleration data to define the FIG. 2 graph, apparatus of the present invention may then be used interactively to access the acceleration data and to compute coefficients of friction at selected times.

The data recorded just as the block is stopping is used to compute the static coefficient of friction if the user moves the cursor to the graph 66 and selects a time point near the point having the largest magnitude of deceleration. A data point selected between 64 and 66 on the plot may be used in computing the kinetic coefficient of friction for determining kinetic coefficients. An embodiment of the invention for determining the kinetic coefficient of friction has one Entran model EGE200-50 accelerometer. Other accelerometers are available from Entran Corporation in Fairfield, N.J.

There has been described herein a method and apparatus for acquiring data related to the slipperiness of a test surface, displaying a graphic representation of such data, and interactively accessing selected data points to compute the coefficients of friction for the test surface. It will be apparent to those skilled in the art who have the benefit of this disclosure that a number of variations may be made to the apparatus and method of the present invention. These variations will be within the spirit and scope of the invention which is limited only by the following claims.

What is claimed is:

1. A method of determining the coefficient of dynamic friction of a surface, comprising:
    imparting an impulse to a block standing on the surface and having a bottom surface of a known test material,
    sensing the acceleration of the block at a series of times;
    generating a series of analog signals proportional to the instantaneous acceleration of the block, each analog signal being generated at a separate such time;
    converting each analog signal to a digital signal;
    communicating the digital signals to a microprocessor;
    recording the value of each digital signal together with its respective time relative to initially imparting the impulse to the block;
    displaying a plot of acceleration against time using the recorded digital values and their respective times;

selecting a time for which a coefficient of friction is to be computed;

determining an average acceleration at the selected time by using a plurality of recorded digital values of acceleration following the selected time;

computing the coefficient of friction by dividing the computed average acceleration by the acceleration of gravity; and displaying the computed coefficient of friction on the video display.

2. A method as recited in claim 1 wherein selecting a time at which the coefficient is to be computed further comprises entering to the microprocessor a proportional value for the selected time relative to the length of the axis along which the time values are plotted.

3. A method as recited in claim 1 wherein selecting a time further comprises displaying a cursor on the plot to mark the selected time.

4. A method as recited in claim 1 wherein selecting a time further comprises entering a command to the microprocessor to move a cursor to the selected time.

5. A method as recited in claim 2, further comprising:
selecting a second time for which the coefficient is to be computed;
determining an average acceleration at the second time using a plurality of recorded digital values of acceleration following the second time;
computing a second coefficient of friction by dividing the computed average acceleration by the acceleration of gravity; and
displaying the computed second coefficient of friction on the video display.

6. A method as recited in claim 1 wherein the average acceleration at the selected time is computed using about 16 acceleration values following the selected time.

7. A method as recited in claim 1 wherein the average acceleration at the selected time is computed using a first plurality of acceleration values immediately preceding the selected time and a second plurality of acceleration values immediately following the selected time.

8. A method of determining the coefficient of friction from series of values from a set of acceleration values which represent the instantaneous accelerations of a weighted block moving on a surface, comprising:
displaying on a video display a plot of the instantaneous accelerations against time;
selecting a time at which a coefficient of friction is to be computed;
computing the coefficient of friction by dividing the instantaneous acceleration at the selected time by the acceleration of gravity; and
displaying the computed coefficient of friction on the video display.

9. A method as recited in claim 8 wherein selecting a time further comprises positioning a cursor on the video display at the time at which the coefficient is to be computed.

10. A method as recited in claim 8, further comprising:
selecting a new point for which the coefficient is to be computed;
computing another coefficient of friction by dividing the instantaneous acceleration at the selected new point by the acceleration of gravity; and
displaying the computed coefficient of friction on the video display.

11. A method as recited in claim 8 wherein the instanteous acceleration is computed as the average of a plurality of acceleration values from a set of acceleration values following the selected time.

12. Apparatus for computing the coefficients of friction of a surface, comprising:
a test block having a bottom surface of a standard test material;
an accelerometer connected to the test block;
an analog to digital converter adapted to receive analog signals from the accelerometer and convert the analog signals into digital signals;
a visual display device upon which the digital signals are plotted;
a microprocessor adapted to receive and store digital signals from the converter and to plot the digital signals on the display device;
means to select a point on the plot for which the coefficient of friction is to be computed; and
means to compute the coefficient of friction at the selected point and display the computed value on the visual display.

13. Apparatus for computing the coefficient of friction of a surface as recited in claim 12 further comprising an instrumentation amplifier to increase the gain of the analog signal communicated to the converter.

14. Apparatus as recited in claim 12 wherein the means to select is a computer program to display a cursor and to move the cursor horizontally to a point on the display device relative to the plotted signals.

15. Apparatus for computing the coefficient of friction at a surface as recited in claim 12 wherein the accelerometer is responsive to substantially constant acceleration; and further comprising:
a second accelerometer responsive to rapid changes in acceleration; and
means to evaluate analog signals from the accelerometers and reject spurious signals.

* * * * *